United States Patent
Stolka et al.

(10) Patent No.: US 11,534,243 B2
(45) Date of Patent: Dec. 27, 2022

(54) SYSTEM AND METHODS FOR NAVIGATING INTERVENTIONAL INSTRUMENTATION

(71) Applicant: Clear Guide Medical, Inc., Baltimore, MD (US)

(72) Inventors: Philipp Jakob Stolka, Baltimore, MD (US); Pezhman Foroughi, Towson, MD (US); Ehsan Basafa, Cockeysville, MD (US); Martin Hossbach, Berlin (DE)

(73) Assignee: CLEAR GUIDE MEDICAL, INC., Baltimore, MD (US)

( * ) Notice: Subject to any disclaimer, the term of this patent is extended or adjusted under 35 U.S.C. 154(b) by 672 days.

(21) Appl. No.: 16/463,174

(22) PCT Filed: Nov. 21, 2017

(86) PCT No.: PCT/US2017/062881
§ 371 (c)(1),
(2) Date: May 22, 2019

(87) PCT Pub. No.: WO2018/098196
PCT Pub. Date: May 31, 2018

(65) Prior Publication Data
US 2019/0374290 A1 Dec. 12, 2019

Related U.S. Application Data

(60) Provisional application No. 62/426,050, filed on Nov. 23, 2016.

(51) Int. Cl.
*A61B 34/20* (2016.01)
*A61B 1/00* (2006.01)
(Continued)

(52) U.S. Cl.
CPC .......... *A61B 34/20* (2016.02); *A61B 1/00009* (2013.01); *A61B 1/053* (2013.01); *A61B 8/5207* (2013.01); *A61B 2034/2065* (2016.02)

(58) Field of Classification Search
CPC ..... A61B 34/20; A61B 1/00009; A61B 1/053; A61B 8/5207; A61B 2034/2065;
(Continued)

(56) References Cited

U.S. PATENT DOCUMENTS 5,836,869 A * 11/1998 Kudo ................... A61B 90/92
600/173
6,036,637 A * 3/2000 Kudo ................. A61B 1/00039
600/102
(Continued)

FOREIGN PATENT DOCUMENTS

WO 2016-168839 A1 10/2016

OTHER PUBLICATIONS

International Search Report from International Application No. PCT/US2017/062881, dated Feb. 22, 2018.
(Continued)

*Primary Examiner* — Alexandra L Newton
*Assistant Examiner* — Shankar Raj Ghimire
(74) *Attorney, Agent, or Firm* — Cahn & Samuels, LLP

(57) ABSTRACT

An image guided surgical system includes a marker attachable to and removable from an elongated surgical tool having a shaft, and at least one camera, and an image processing system in communication with the camera configured to obtain an image of the surgical tool. The image processing system is configured to operate in a calibration mode to generate a template and display the template on a display device and to receive a user input, after the image of the surgical tool is aligned to the template, to adjust a length of the template to substantially match a length of the surgical tool. A storage device in communication with the image processing system is included to store calibration information that associates a position of the marker with a position (Continued)

of the tip of the shaft of the surgical tool based on the adjusted length of the template.

13 Claims, 5 Drawing Sheets

(51) Int. Cl.
 *A61B 1/05* (2006.01)
 *A61B 8/08* (2006.01)
(58) Field of Classification Search
 CPC .......... A61B 2017/00725; A61B 90/39; A61B 2034/2055; A61B 2090/365; A61B 2090/364; A61B 2090/3937; A61B 2090/3983
 See application file for complete search history.

(56) References Cited

U.S. PATENT DOCUMENTS

| | | | | |
|---|---|---|---|---|
| 6,216,029 | B1* | 4/2001 | Paltieli | A61B 34/20 600/427 |
| 8,073,528 | B2* | 12/2011 | Zhao | A61B 1/00193 600/424 |
| 8,108,072 | B2* | 1/2012 | Zhao | G06K 9/3216 700/250 |
| 8,666,476 | B2* | 3/2014 | Yamamoto | A61B 34/20 600/424 |
| 8,880,151 | B1* | 11/2014 | Stolka | A61B 8/4254 600/424 |
| 2003/0078502 | A1* | 4/2003 | Miyaki | A61B 10/04 600/461 |
| 2004/0019274 | A1* | 1/2004 | Galloway, Jr. | A61B 34/20 600/425 |
| 2005/0084833 | A1 | 4/2005 | Lacey et al. | |
| 2005/0085717 | A1* | 4/2005 | Shahidi | A61B 8/0841 600/424 |
| 2005/0090742 | A1* | 4/2005 | Mine | A61B 34/20 600/443 |
| 2005/0273004 | A1 | 12/2005 | Simon et al. | |
| 2008/0015664 | A1* | 1/2008 | Podhajsky | A61B 34/10 607/99 |
| 2008/0064952 | A1 | 3/2008 | Li et al. | |
| 2010/0168562 | A1* | 7/2010 | Zhao | A61B 90/94 600/426 |
| 2010/0298705 | A1* | 11/2010 | Pelissier | A61B 8/42 600/443 |
| 2011/0282188 | A1* | 11/2011 | Burnside | A61B 8/4254 600/424 |
| 2011/0295108 | A1* | 12/2011 | Cox | A61B 5/063 600/424 |
| 2015/0272700 | A1* | 10/2015 | Masuda | A61B 34/20 600/424 |
| 2016/0081653 | A1* | 3/2016 | Masuda | A61B 8/4254 600/424 |
| 2017/0188991 | A1* | 7/2017 | Boctor | A61B 1/00 |
| 2017/0354315 | A1* | 12/2017 | Saito | G06T 7/0012 |
| 2017/0354320 | A1* | 12/2017 | Saito | A61B 1/05 |
| 2018/0325610 | A1* | 11/2018 | Cameron | A61B 5/1079 |
| 2019/0201110 | A1* | 7/2019 | Kuenen | G06T 5/50 |
| 2019/0204069 | A1* | 7/2019 | Tatsuta | G01B 11/028 |
| 2019/0380794 | A1* | 12/2019 | Al Jewad | A61B 17/7082 |
| 2019/0388161 | A1* | 12/2019 | Cicchini | A61B 34/20 |

OTHER PUBLICATIONS

Written Opinion from International Application No. PCT/US2017/062881, dated Feb. 22, 2018.
Fischer et al., "MRI image overlay application to arthrography needle insertion", Computer Aided Surgery, vol. 12, No. 1, pp. 2-14, 2017.

* cited by examiner

FIG. 3A
(CONVENTIONAL)
FIG. 3B
(CONVENTIONAL)

SYSTEM AND METHODS FOR NAVIGATING INTERVENTIONAL INSTRUMENTATION

CROSS-REFERENCE TO RELATED APPLICATIONS

This application is a National Stage Application under 35 U.S.C. § 371 PCT/US2017/062881, filed on Nov. 21, 2017, which claims priority benefit from U.S. Provisional Patent Application No. 62/426,050 filed on Nov. 23, 2016, the entire content of each is incorporated herein by reference.

BACKGROUND

1. Technical Field

This disclosure generally relates to image systems for navigating surgical medical devices. More particularly, this disclosure relates to a system and methods for navigating interventional instrumentation, such as surgical needles, involving image identification and tracking of unique tags and/or graphical patterns associated with or attached to interventional instrumentation.

2. Discussion of Related Art

In the course of performing a surgical operation or intervention, a medical practitioner (e.g., a surgeon) may use various operating instruments to perform various operations such as needle biopsies, tumor ablations, catheter insertion, orthopedic interventions, etc. These instruments may use several types of image data to aid the medical practitioner or operator in inserting the instrument into a desired location within a patient's body. Typically, the medical practitioner inserts these instruments into a patient's body at very specific locations, orientations, and depths to reach predetermined target areas in order to perform an instrument-specific action or function, which may include tissue sampling, heating, cooling, liquid deposition, suction, or serving as a channel for other objects.

Correct placement of such interventional instruments is a challenge under typical conditions. Operators rely on external visual or tactile feedback (e.g., number of centimeter (cm) markings on the needle disappeared inside the tissue, or sensation of membrane penetration), or use one or more imaging modalities (e.g., ultrasound, Computed Tomography (CT), Cone Beam Computed Tomography (CBCT), Magnetic Resonance Imaging (MRI), and the like) to guide said instrument placement.

Medical navigation systems based on a variety of different tracking technologies (mechanical, infrared-optical, electromagnetic, etc.) have existed for a long time, and help with aligning patient, targets, and instruments. However, the known medical navigation systems remain inaccurate, inconvenient, and ineffective in providing real-time data and guidance in inserting and moving interventional instruments.

Therefore, a need remains for improved systems and methods for navigating interventional medical instrumentation.

SUMMARY OF THE DISCLOSURE

An aspect of the present disclosure is to provide an image guided surgical system including a marker attachable to and removable from an elongated surgical tool having a shaft and at least one camera. The image guided surgical system further includes an image processing system in communication with the camera configured to obtain an image of the surgical tool including the marker and a display device in communication with the image processing system. The display device is configured to display the image of the surgical tool including the marker. The image processing system is configured to operate in a calibration mode to generate a template and display the template on the display device and to receive a user input, after the image of the surgical tool is aligned to the template, to adjust a length of the template to substantially match a length of the surgical tool. The image guided surgical tool also includes a storage device in communication with the image processing system. The storage device is configured to store calibration information that associates a position of the marker with a position of the tip of the shaft of the surgical tool based on the adjusted length of the template.

BRIEF DESCRIPTION OF THE DRAWINGS

The present disclosure, as well as the methods of operation and functions of the related elements of structure and the combination of parts and economies of manufacture, will become more apparent upon consideration of the following description and the appended claims with reference to the accompanying drawings, all of which form a part of this specification. Like reference numerals designate corresponding parts in the various figures. The drawings are for the purpose of illustration and description only and are not intended as a definition of the limits of the invention.

FIG. 3A depicts a conventional needle without any markings used in an intervention procedure;

FIG. 3B depicts another conventional needle having a non-repeating binary pattern on the shaft of the needle;

DETAILED DESCRIPTION

This disclosure concerns with a medical-device system and methods that allow operators to perform navigation-assisted interventions using certain types of intervention instruments, such as needle-like instruments, and corresponding methods of tracking the instruments with certain attached markers and calibrating the system to enable tracking the instruments.

Clear Guide Medical has previously developed a novel visual tracking technology platform based on real-time camera-based computer vision, and embodied it in products for ultrasound- and CT-based systems for image/instrument guidance and multi-modality fusion Certain aspects of this technology has been already described in U.S. patent application Ser. No. 13/648,245, U.S. patent application Ser. No. 14/092,755, U.S. patent application Ser. No. 14/092,843, U.S. patent application Ser. No. 14/508,223, U.S. patent application Ser. No. 14/524,468, U.S. patent application Ser. No. 14/524,570, and U.S. patent application Ser. No. 14/689,849, the entire content of each being incorporated herein by reference.

Figure 1:
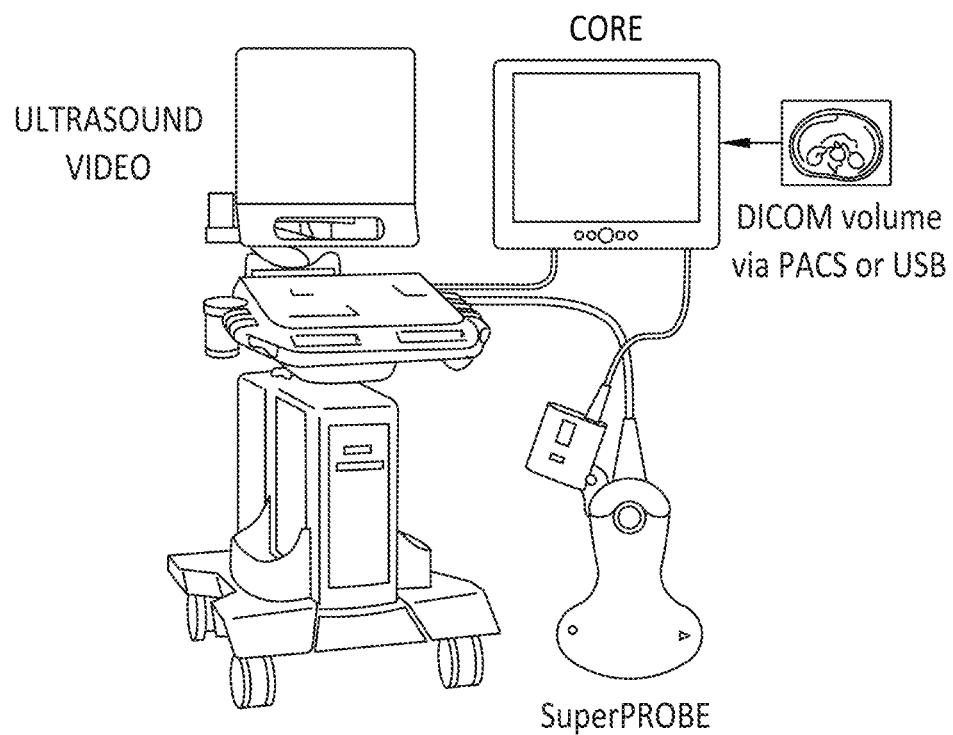
FIG. 1 depicts an example of an ultrasound system (e.g., Clear Guide SCENERGY system) having an ultrasound probe having mounted thereon a tracking device (e.g., one or more cameras) for tracking a position of an interventional or surgical tool when operating on a patient's body, according to an embodiment of the present disclosure.

FIG. 1 depicts an example of an ultrasound system (e.g., Clear Guide SCENERGY system) having an ultrasound probe having mounted thereon a tracking device (e.g., one or more cameras) for tracking a position of an interventional or surgical tool when operating on a patient's body, according to an embodiment of the present disclosure. One or more cameras image objects in their field of view, detect and localize reference features for registration and tracking, reconstruct their poses in camera space, and register them to corresponding objects' poses in other image data sets. As it will described further in detail in the following paragraphs, the ultrasound system can be configured in accordance with embodiments of the present disclosure for navigating interventional instrumentation, such as surgical needles, and refining registration between image modalities.

Figure 2:
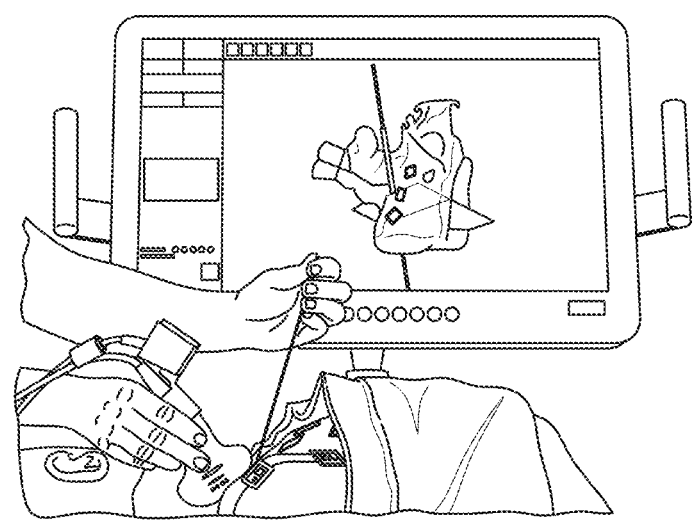
FIG. 2 depicts a health practitioner inserting a needle into a patient's body while using an ultrasound system (e.g., Clear Guide Medical "SCENERGY" system) having the one or more cameras to track the position of the needle relative to patient's body, the ultrasound system providing an image displaying information about a path of the needle insertion within the patient's body, according to an embodiment of the present disclosure.

FIG. 2 depicts a health practitioner inserting a needle into a patient's body while using an ultrasound system (e.g., Clear Guide Medical "SCENERGY" system) having the one or more cameras to track the position of the needle relative to patient's body, the ultrasound system providing an image displaying information about a path of the needle insertion within the patient's body. The Clear Guide "SCENERGY" system allows fusion of registration images of ultrasound and CT devices based on skin-attached "VisiMARKER" fiducials. These multi-modality markers comprise a radiopaque layer that is automatically segmented from radiographic imaging based on its known high intensity, and a visible checkerboard-like surface pattern that allows observing cameras to localize the marker in six degrees of freedom in camera coordinates (see also Olson E., AprilTag: A robust and flexible visual fiducial system, IEEE-ICRA 2011, the entire content of which is incorporated herein by reference).

The above systems can be used to detect a position of instruments such as straight, rigid, needle-like tools, including needles, biopsy guns, ablation tools, etc. For example, a non-repeating binary pattern is provided on the instrument that allows the system to visually track the instrument tip without seeing the latter directly, by estimating the distance to the tip from any unique observed pattern sub-sequence. Such system is described in U.S. patent application Ser. No. 14/092,843 to Stolka et al., the entire content of which is incorporated herein by reference. FIG. 3A depicts a conventional needle without any markings used in an intervention procedure. In this example, the medical practitioner relies on imaging techniques such as ultrasound and tactile feedback to visually track the tip of the needle. FIG. 3B depicts a conventional needle having a non-repeating binary pattern on the shaft of the needle. In this example, the system tracks the instrument tip without seeing the latter directly by estimating the distance to the tip from the unique observed pattern sub-sequence (e.g., observed by the camera of the system). A detailed description of such needle is provided in U.S. Pat. No. 9,668,819 to Stolka et al., the entire content of which is incorporated herein by reference.

Figure 3C:
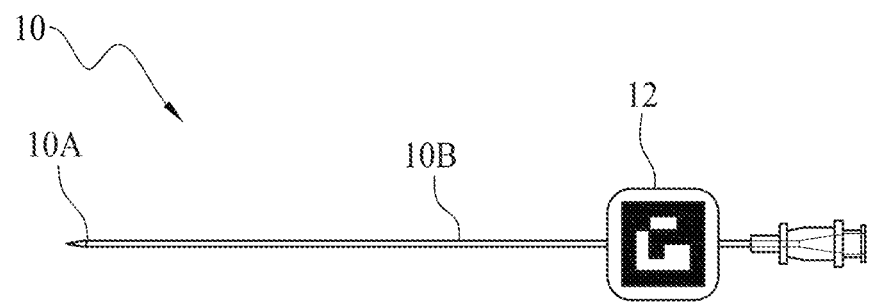
FIG. 3C depicts a needle configuration having a marker or a tag, according to an embodiment of the present disclosure.

FIG. 3C depicts a needle 10 configuration having a marker or a tag 12, according to an embodiment of the present disclosure. The marker or tag 12 is referred to herein as "TipTAG" in that, although not located on the tip 10A of the instrument (e.g., needle), the marker or tag 12 allows tracking the tip 10A of the needle 10. In an embodiment, the TipTAG marker 12 is attached to the shaft 10B of the needle 10 at a certain distance from the tip 10A. This configuration allows operators to enable tip tracking across all pre-existing needle-like instruments. Localization of these instruments is performed not only using the geometric properties of their shafts, but also those of attached markers that are visible to the system camera(s). The TipTAG marker 12 can have any shape. For example, as shown in FIG. 3C, the TipTAG marker 12 has a square shape. However, the TipTAG marker 12 can have any polygonal shape (a triangle, square, rectangle, pentagon, hexagon, etc.) or a circular or elliptical shape or more complex shape.

In an embodiment, TipTAG markers can include single-use or multiple-use markers that can be permanently or removably attached to an interventional instrument, such as a surgical needle, a biopsy tool, a laparoscope, an ablation device, etc. Although a straight type needle is depicted in FIG. 3C, the interventional instrument can be a straight needle-like tool, steerable needle, bended or bendable needle, and the like. The TipTAG markers include a graphical element, such as a predetermined pattern or image, that can be recognized by the system employing image processing. Accordingly, the TipTAG marker can serve as an identification tag attachable to interventional instruments for their tracking. Each TipTAG marker can have a unique graphical element enabling the system to differentiate two or more TipTAG markers and, optionally, obtain certain information about the interventional instruments having TipTAG markers attached thereto. The TipTAG marker can have any shape.

Figure 4:
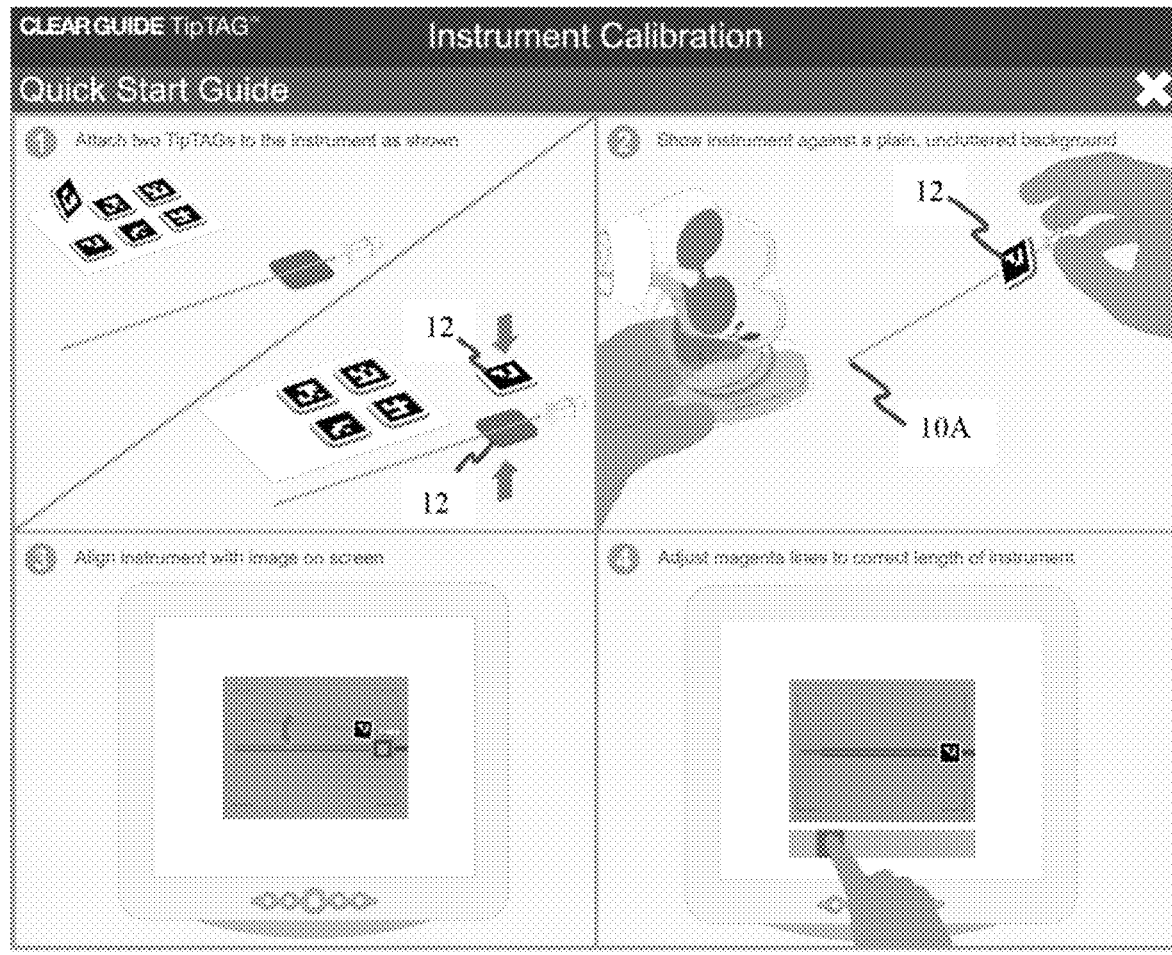
FIG. 4 depicts some aspects of a calibration procedure for calibrating an image processing system to associate the marker with the dimensional characteristics of the surgical tool, according to an embodiment of the present disclosure.

In operation, the TipTAG markers can be calibrated to an instrument tip using the system. FIG. 4 depicts some aspects of a calibration procedure for calibrating an image processing system to associate the TipTAG marker with the dimensional characteristics of the surgical tool, according to an embodiment of the present disclosure. At step 1, a TipTAG marker 12 is attached to an interventional instrument (e.g., a needle) 10. For example, an operator may attach one or more TipTAG markers 12 (for example, two TipTAG markers opposite to each other), as shown in the upper left quadrant of FIG. 4. At step 2, the system captures images of the interventional instrument 10 with the TipTAG marker 12 attached thereto, as shown in the upper right quadrant of FIG. 4. At step 3, the system identifies the TipTAG marker 12, displays an image or a real-time video of TipTAG marker 12 and a generated shape pattern or template. The shape pattern or template includes an outline of the interventional instrument 10. At step 3, an operator moves and adjusts the interventional instrument 10 so as to align an image of the interventional instrument 10 with the generated template, as shown in the lower left quadrant of FIG. 4. At step 4, a length of the template is adjusted so that the length of the template substantially matches an actual length of the interventional tool 10. At step 4, the system acquires the adjusted length of the interventional instrument so that the length of the template substantially matches the actual length of the interventional instrument 10, as shown in the lower right quadrant of FIG. 4. After the calibration, the system associates the TipTAG marker 12 with dimensional characteristics of the interventional instrument 10 and optionally other parameters such as a type of needle, make, shape, design, color, and so forth.

In an embodiment, the calibration procedure further establishes the geometrical six Degrees of Freedom (6-DoF) transformation between the instrument shaft 10B and the instrument tip 10A, and the attached marker(s) 12. For example, for straight needles, no long-axis rotation can be observed/defined, but for other instrument shaft shapes (e.g., a curved shaft) full 6 degrees of freedom are captured by the calibration above. The desired system behavior is the real-time display of needle shaft 10B whenever the shaft 10B or part of the shaft 10B is visible and display the needle tip 10A 9 (or a representation of the needle tip 10A) whenever an attached TipTAG marker 12 is observed.

Figure 5:
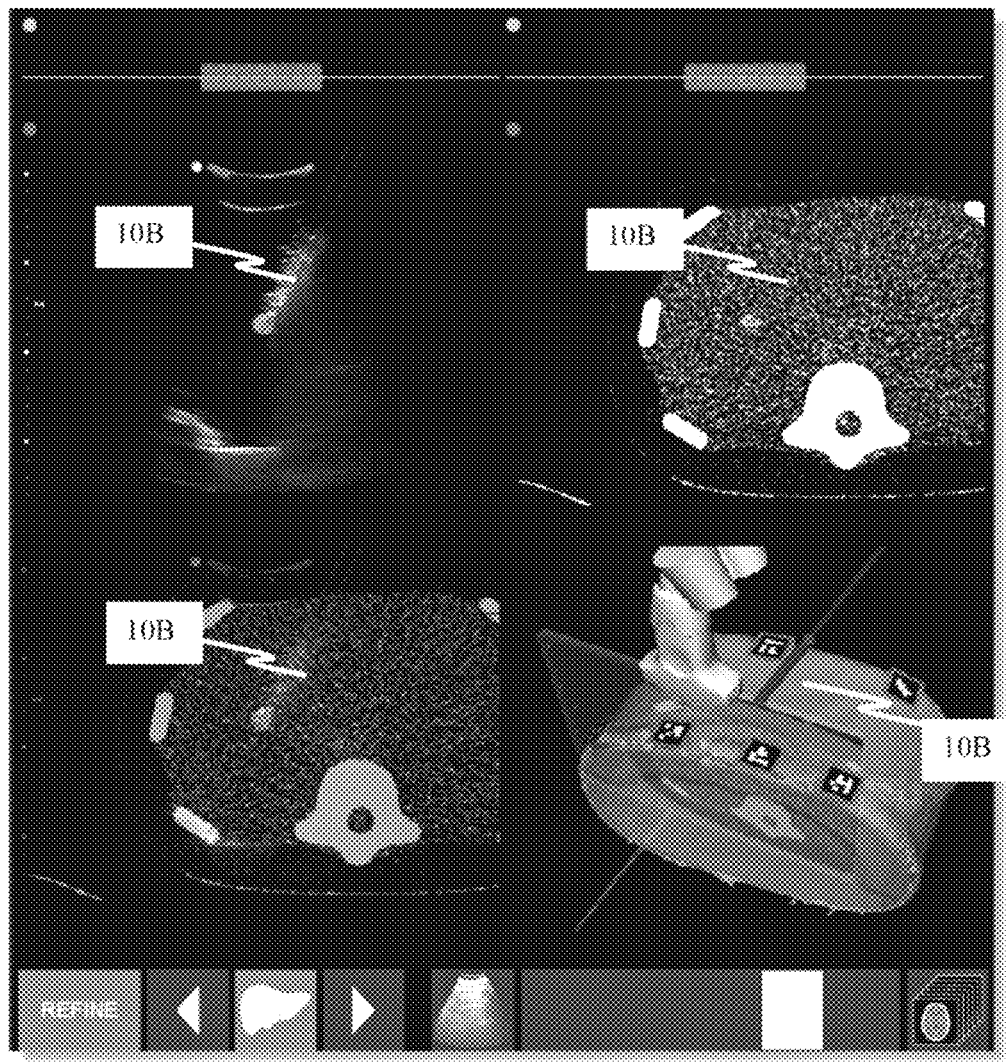
FIG. 5 depicts a display system showing a tip-tracked instrument overlays on four different visualizations: ultrasound, CT, fusion, and 3D views, according to various embodiments of the present disclosure.

FIG. 5 depicts a display system showing a tip-tracked instrument overlays on four different visualizations: ultrasound, CT, fusion, and 3D views, according to various embodiments of the present disclosure. The upper left quadrant of FIG. 5 shows an ultrasound image with two parallel lines representing the shaft 10B of the interventional tool (e.g., needle) 10. The upper right quadrant of FIG. 5 shows a CT scan image with two parallel lines representing the shaft 10B of the interventional tool (e.g., needle) 10. The lower left quadrant of FIG. 5 shows a fusion image (wherein the CT scan and the ultrasound images are fused or merged) with two parallel lines representing the shaft 10B of the interventional tool (e.g., needle) 10. The lower right quadrant of FIG. 5 shows a 3D view with a representation of the shaft 10B of the interventional tool (e.g., needle) 10.

In an embodiment, the tagged interventional instrument 10 tagged with TipTAG marker 12 can be used in any imaging system using a camera system that is configured to acquire an image of one or more TipTAG marker 12. As it can be understood, the one or more TipTAG markers 12 can be positioned at various locations of the interventional instrument 10 such that the camera is able to capture an image of at least one of the one or more TipTAG markers during the manipulation or the operation of the interventional instrument 10 so that the tip 10A of the interventional instrument 10 can be located.

In an embodiment, 6-DoF localization of markers based on camera images can be used, for example (Method A). A detailed description of an example of such system and method can be found in U.S. patent application Ser. No. 14/689,849 to Stolka et al., the entire content of which is incorporated herein by reference. In an embodiment, a camera-based needle pose estimation can be implemented, for example, using the system described in "Stolka et al., Navigation with Local Sensors in Handheld 3D Ultrasound: Initial in-vivo Experience, SPIE MI 2011," the entire content of which is also incorporated herein by reference (Method B). In an embodiment, optionally, a vision-based tip location estimation for more precise localization, or approximatively via discontinuity detection along the detected instrument shaft line can be also employed (Method C).

In an embodiment, the following components allow to determine the desired TipTAG calibration:

1. Determine 6-DoF (six-degree of freedom) marker pose M_1.
2. Determine 5-DoF (five-degree of freedom) instrument shaft and tip pose M_2 (directly using Method C), or using Method B with possible manual corrective input (as illustrated in FIG. 4, lower right quadrant). Set arbitrary long-axis orientation.
3. Determine TipTAG marker-to-tip calibration as M=M_2*inv(M_1).

In an embodiment, the above calibration may be performed based on a single image n-tuple (ideally n≥2 to simplify Method B). Although, under certain conditions, this may also be performed using a monocular setup, for example as described in "Single-Camera Closed-Form Real-Time Needle Tracking for Ultrasound-Guided Needle Insertion" by Najafi et al., Ultrasound in Medicine & Biology 2015, the entire content of which is incorporated herein by reference. However, integrating the results of this procedure from multiple viewing angles of the same TipTAG instrument (e.g. simple transformation averaging) may improve accuracy and confidence.

It should be noted that setting an arbitrary long-axis orientation may be appropriate only for rotationally-invariant instruments such as straight needles. For others shapes of needles, such as bent or asymmetrical needles, steerable instruments, or other kinds of elongated instruments, full-6-DoF direct shape reconstruction, and tip detection along a reconstructed shape, enables full 6-DoF instrument tracking. This reconstruction can be implemented using n-ocular vision (for n≥2) and continuous disparity tracking along the detected 3D shaft, e.g. by region-growing the longest detected linear shape extending from the detected marker. In addition, dynamic shape changes, e.g., for steerable instruments, extensible cannulas etc., may be integrated into the 6-DoF tracking approach if these shape changes can be modelled relative to the initial reconstructed shape based on observable instrument features or other external system inputs, such as instrument control information.

In an embodiment, if a problem occurs wherein the system is not able determine the location of the tip 10A of the instrument 10 as the marker 12 is not (or not yet, depending on insertion depth) visible in any camera viewing cones, then, the system can revert to regular instrument localization, i.e. without tip tracking, as a "fail-safe" method. To avoid this potential loss of interventional information, instrument types can be combined, for example, by placing the TipTAG marker 12 on an instrument having a non-repeating binary pattern on the shaft of the instrument. This can be accomplished by applying the TipTAG marker 12 to the interventional instrument (e.g., needle), shown in FIG. 3B, having the non-repeating binary pattern on the shaft. This allows for continuous instrument-and-tip tracking during the whole (typically downwards) passage through the camera viewing cones. For example, during the sequence wherein only the shaft is visible, the shaft and TipTAG marker are visible, only short shaft segment and the TipTAG marker are visible, and only the marker is visible.

In an embodiment, a shaft pattern learning approach may also be combined with the application of a TipTAG marker to enhance tip localization whenever the marker can be observed, independent of the visibility of any shaft patterning. For example, this can be employed in the tracking of an instrument whose shaft has only suboptimal patterning, such as for example 1/1/1/1/5/1/1/1/1/10/ . . . cm rings or other semi-irregular markings. In this example, the pattern is non-repeating so that any non-negligible sub-sequence is unique, but many sub-sequences of substantial length may not (i.e., they are identical to each other, e.g. the repeating instances of "1/1/1/1"). Such lesser semi-irregular markings can still be used to quasi-localize the instrument tip along a shaft up to certain equivalence groups. These equivalence groups contain "tip location hypotheses," and depend on the underlying pattern and the actually observed subsequence. For example, observing "1/1/1" from the pattern above can indicate the presence of the tip 1, 2, 6, or 7 units to the left. Whereas, observation of "5" uniquely localizes the tip 5 units to the left. The observed pattern can be brute-force correlated onto the semi-irregular markings to produce tip quasi-localizations whenever it matches. The semi-irregular markings themselves may be known a priori like a non-repeating binary pattern, or may be learned by the system via camera observations analogous to the TipTAG calibration method.

Example: Monocular and Multimodality Augmented Reality (MOAMMAR): The TipTAG instrument tracking method enables reliable and precise monocular instrument localization, without additional requirements as to instrument properties or poses. For example, an imaging system (e.g., CLEARGUIDE imaging system) variation may fuse real-time monocular video and overlays generated from pre-operative CT scan data (such as segmented bones or orthogonal slices through target locations shown in FIGS. 6A and 6B) into an augmented reality (AR) view. This may be implemented in a handheld form factor, such as a tablet computer with integrated camera, as shown in FIG. 6A.

Figure 6A:
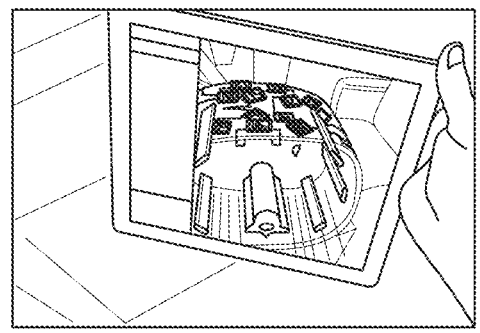
FIG. 6A depicts a handheld computer system using monocular vision to create Augmented Reality (AR) overlays of CT scan data with instrument position from real-time monocular video, according to an embodiment of the present disclosure.

FIG. 6A depicts a handheld computer system using monocular vision to create Augmented Reality (AR) overlays of CT scan data with instrument position from real-time monocular video, according to an embodiment of the present disclosure. For example, TipTAG instruments can be localized precisely and overlaid onto a camera view. Their poses can also serve to decide what image data to use to generate the static-image overlays, more precisely to determine the slice or directional view to extract from a static image volume. For example, a variable CT slice that simultaneously contains a given target and the tracked instrument shaft may be extracted and overlaid. While this monocular scenario is enabled in particular by the TipTAG instrument marker approach, the stereo camera head described above may be used as well in other embodiments.

Figure 6B:
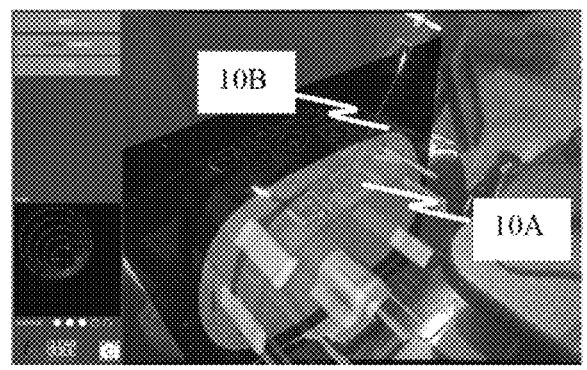
FIG. 6B depicts a screen view including additional image, instrument and tip tracking, and target features, according to an embodiment of the present disclosure.

FIG. 6B depicts a screen view including additional image, instrument and tip tracking, and target features, according to an embodiment of the present disclosure. The position of a representation of the instrument shaft 10B and the tip 10A of the instrument 10, obtained using the above TipTAG instrument marker approach, are overlaid on top of an image from the CT scan data.

As it can be appreciated from the above paragraphs, there is provided an image guided surgical system. The image guided surgical system includes a marker attachable to and removable from an elongated surgical tool having a shaft, such as but not limited to, a needle, and at least one camera. The image guided surgical system further includes an image processing system in communication with the camera configured to obtain an image of the surgical tool including the marker. The image guided surgical system also includes a display device in communication with the image processing system. The display device is configured to display the image of the surgical tool including the marker. The image processing system is configured to operate in a calibration mode to generate a template and display the template on the display device and to receive a user input, after the image of the surgical tool is aligned to the template, to adjust a length of the template to substantially match a length of the surgical tool. The image guided surgical system further includes a storage device in communication with the image processing system. The storage device is configured to store calibration information that associates a position of the marker with a position of the tip of the shaft of the surgical tool based on the adjusted length of the template.

In an embodiment, the image processing system once calibrated is configured, in an operating mode, to determine the position of a tip of the shaft of the surgical tool based on a captured image of the marker and using the stored calibration information. In an embodiment, the shaft of the surgical tool including the tip is displayed on the display device as a phantom image superposed to a medical image, wherein the position of the tip is determined based on the captured image of the marker. In an embodiment, the medical image includes a CT scan image, an ultrasound image, a 3D representation of a body of a patient, or a combination thereof.

In an embodiment, the image processing system is configured to construct the phantom image of the surgical tool based upon the captured images of the surgical tool and based upon six degrees of freedom positional information of the surgical tool and the position of the marker. In an embodiment, the image processing system is further configured to overlay the constructed phantom image of the surgical tool on a real-time medical image of a patient so as to enable a user to track a position of at least the tip of the shaft when inserted into the patient.

In an embodiment, the marker has encoded therein a type of the surgical tool, make of the surgical tool, shape of the surgical tool, design of the surgical tool, color of the surgical tool, or any combination thereof. The marker may also include unique graphical elements, patterns, symbols, or shapes that differentiate the marker from other markers.

In an embodiment, the surgical tool can be, for example, a needle or other elongated surgical tool. The marker can be attachable to or removable from a shaft of the needle. In an embodiment, the shaft of the needle comprises a pattern (for example, as shown in FIG. 3B).

In an embodiment, the image guided surgical system may include a plurality of markers, each having distinct graphical elements, patterns, symbols or shapes (such as the markers shown in FIG. 4, upper left quadrant) and configured to be attached to the elongated surgical tool at different locations. For example, the plurality of markers can be placed at different locations of the elongated surgical tool so that the one or more cameras can capture at least one of the plurality of the markers when the elongated surgical tool is used by a medical practitioner during a medical operation.

The foregoing detailed description of embodiments includes references to the drawings or figures, which show illustrations in accordance with example embodiments. The embodiments described herein can be combined, other embodiments can be utilized, or structural, logical and operational changes can be made without departing from the scope of what is claimed. The foregoing detailed description is, therefore, not to be taken in a limiting sense, and the scope is defined by the appended claims and their equivalents. It should be evident that various modifications and changes can be made to these embodiments without departing from the broader spirit and scope of the present disclosure. Accordingly, the specification and drawings are to be regarded in an illustrative rather than a restrictive sense.

Present teachings may be implemented using a variety of technologies. For example, certain aspects of this disclosure may be implemented using electronic hardware, computer software, or any combination thereof. Whether such elements are implemented as hardware or software depends upon the particular application and design constraints imposed on the overall system. By way of example, the electronic hardware, or any portion of electronic hardware may be implemented with a processing system that includes one or more processors. Examples of processors include microprocessors, microcontrollers, Central Processing Units (CPUs), digital signal processors (DSPs), field programmable gate arrays (FPGAs), programmable logic devices (PLDs), state machines, gated logic, discrete hardware circuits, and other suitable hardware configured to perform various functions described throughout this disclosure. One or more processors in the processing system may execute software, firmware, or middleware (collectively referred to as "software"). The term "software" shall be construed broadly to mean instructions, instruction sets, code, code segments, program code, programs, subprograms, software components, applications, software applications, software packages, routines, subroutines, objects, executables, threads of execution, procedures, functions, etc., whether referred to as software, firmware, middleware, microcode, hardware description language, or otherwise. In certain embodiments, the electronic hardware can also include designed application-specific integrated circuits (ASICs), programmable logic devices, or various combinations thereof. The processing system can refer to a computer (e.g., a desktop computer, tablet computer, laptop computer), cellular phone, smart phone, and so forth. The processing system can also include one or more input devices, one or more output devices (e.g., a display), memory, network interface, and so forth.

If certain functions described herein are implemented in software, the functions may be stored on or encoded as one or more instructions or code on a non-transitory computer-readable medium. Computer-readable media includes computer storage media. Storage media may be any available media that can be accessed by a computer. By way of example, and not limitation, such computer-readable media can comprise a random-access memory (RAM), a read-only memory (ROM), an electrically erasable programmable ROM (EEPROM), compact disk ROM (CD-ROM) or other optical disk storage, magnetic disk storage, solid state memory, or any other data storage devices, combinations of the aforementioned types of computer-readable media, or any other medium that can be used to store computer executable code in the form of instructions or data structures that can be accessed by a computer.

For purposes of this patent document, the terms "or" and "and" shall mean "and/or" unless stated otherwise or clearly intended otherwise by the context of their use. The term "a" shall mean "one or more" unless stated otherwise or where the use of "one or more" is clearly inappropriate. The terms "comprise," "comprising," "include," and "including" are interchangeable and not intended to be limiting. For example, the term "including" shall be interpreted to mean "including, but not limited to."

Although embodiments have been described with reference to specific example embodiments, it will be evident that various modifications and changes can be made to these example embodiments without departing from the broader spirit and scope of the present application. Accordingly, the specification and drawings are to be regarded in an illustrative rather than a restrictive sense.

We claim:

1. An image guided surgical system comprising:
 a marker attachable to and removable from an elongated surgical tool having a shaft;
 at least one camera;
 an image processing system in communication with the camera configured to obtain an image of the surgical tool including the marker;
 a display device in communication with the image processing system, the display device being configured to display the image of the surgical tool including the marker,
 wherein the image processing system is configured to operate in a calibration mode to generate a template and display the template on the display, and wherein the display device is configured to receive a user input to allow an operator to align the image of the surgical tool to the template, and adjust a length of the template to substantially match a length of the surgical tool; and
 a storage device in communication with the image processing system, the storage device being configured to store calibration information that associates a position of the marker with a position of the tip of the shaft of the surgical tool based on the adjusted length of the template.

2. The system according to claim 1, wherein the image processing system once calibrated is configured, in an operating mode, to determine the position of a tip of the shaft of the surgical tool based on a captured image of the marker and using the stored calibration information.

3. The system according to claim 2, wherein the shaft of the surgical tool including the tip is displayed on the display device as a phantom image superposed to a medical image, wherein the position of the tip is determined based on the captured image of the marker.

4. The system according to claim 3, wherein the medical image includes a CT scan image, an ultrasound image, or a combination thereof.

5. The system according to claim 3, wherein the medical image includes a 3D representation of a body of a patient.

6. The system according to claim 2, wherein the image processing system is configured to construct the phantom image of the surgical tool based upon the captured images of the surgical tool and based upon six degrees of freedom of positional information of the surgical tool and the position of the marker.

7. The system according to claim 6, wherein the image processing system is further configured to overlay the constructed phantom image of the surgical tool on a real-time medical image of a patient so as to enable a user to track a position of at least the tip of the shaft when inserted into the patient.

8. The system according to claim 1, wherein the marker has encoded therein a type of the surgical tool, make of the surgical tool, shape of the surgical tool, design of the surgical tool, color of the surgical tool, or any combination thereof.

9. The system according to claim 1, wherein the marker includes unique graphical elements, patterns, symbols, or shapes that differentiate the marker from other markers.

10. The system according to claim 1, wherein the surgical tool is a needle.

11. The system according to claim 10, wherein the marker is attachable to or removable from a shaft of the needle.

12. The system according to claim 11, wherein the shaft of the needle comprises a pattern.

13. The system according to claim 1, further comprising a plurality of markers, each having distinct graphical elements, patterns, symbols or shapes and configured to be attached to the elongated surgical tool at different locations.

* * * * *